United States Patent
Johnson et al.

(10) Patent No.: US 8,115,928 B2
(45) Date of Patent: Feb. 14, 2012

(54) BOX INSPECTOR

(75) Inventors: Aaron C. Johnson, Northfield, NH (US); Philip Mutarelli, Merrimack, NH (US)

(73) Assignee: Graham Packaging Company, L.P., York, PA (US)

( * ) Notice: Subject to any disclaimer, the term of this patent is extended or adjusted under 35 U.S.C. 154(b) by 390 days.

(21) Appl. No.: 12/544,382

(22) Filed: Aug. 20, 2009

(65) Prior Publication Data

US 2011/0043802 A1 Feb. 24, 2011

(51) Int. Cl.
- G01B 11/00 (2006.01)
- G01B 11/14 (2006.01)
- G01B 11/02 (2006.01)
- G01B 11/08 (2006.01)
- G01N 21/00 (2006.01)

(52) U.S. Cl. ........................ 356/394; 356/240.1; 356/625; 356/640

(58) Field of Classification Search .... 356/237.1–241.6, 356/388–398, 600–640
See application file for complete search history.

(56) References Cited

U.S. PATENT DOCUMENTS

| 3,750,877 | A | * | 8/1973 | Dvacho et al. | 209/588 |
| 4,165,939 | A | | 8/1979 | Woodrow et al. | |
| 5,141,111 | A | * | 8/1992 | Licht | 209/558 |
| 5,388,707 | A | | 2/1995 | Stivison et al. | |
| 5,802,803 | A | * | 9/1998 | Kitagawa et al. | 53/54 |
| 5,943,436 | A | * | 8/1999 | Ebel et al. | 382/143 |
| 6,757,420 | B2 | | 6/2004 | Krahn et al. | |
| 2008/0310676 | A1 | | 12/2008 | Silver | |

* cited by examiner

*Primary Examiner* — Gregory J Toatley
*Assistant Examiner* — Jarreas C Underwood
(74) *Attorney, Agent, or Firm* — Stradley Ronon Stevens & Young, LLP

(57) ABSTRACT

A box inspector for detecting at an inspection station an unacceptable skew in, an item missing from, and/or an unacceptable gap in a box. The box inspector has pairs of aligned emitters and receivers generating a signal when an unacceptable skew is detected, at least two item present sensors corresponding to the number of items adapted to be located in a single row within the box and generating an item absent signal when an item is missing from the box, a gap detect sensor generating an unacceptable gap signal when the gap is larger than a predetermined gap size, and a box present sensor generating a box present signal when a box arrives at the inspection station. A controller receives signals from these components and generates indications when the box is unacceptably skewed, an item is missing from the box, and/or an unacceptable gap exists in the box.

20 Claims, 7 Drawing Sheets

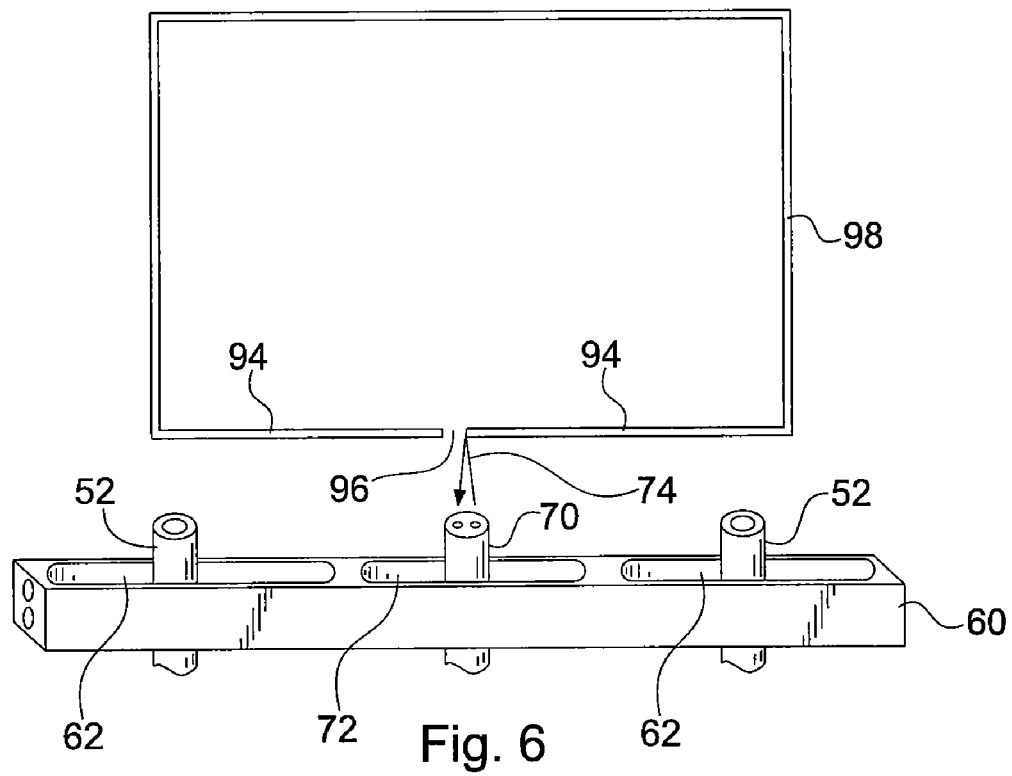
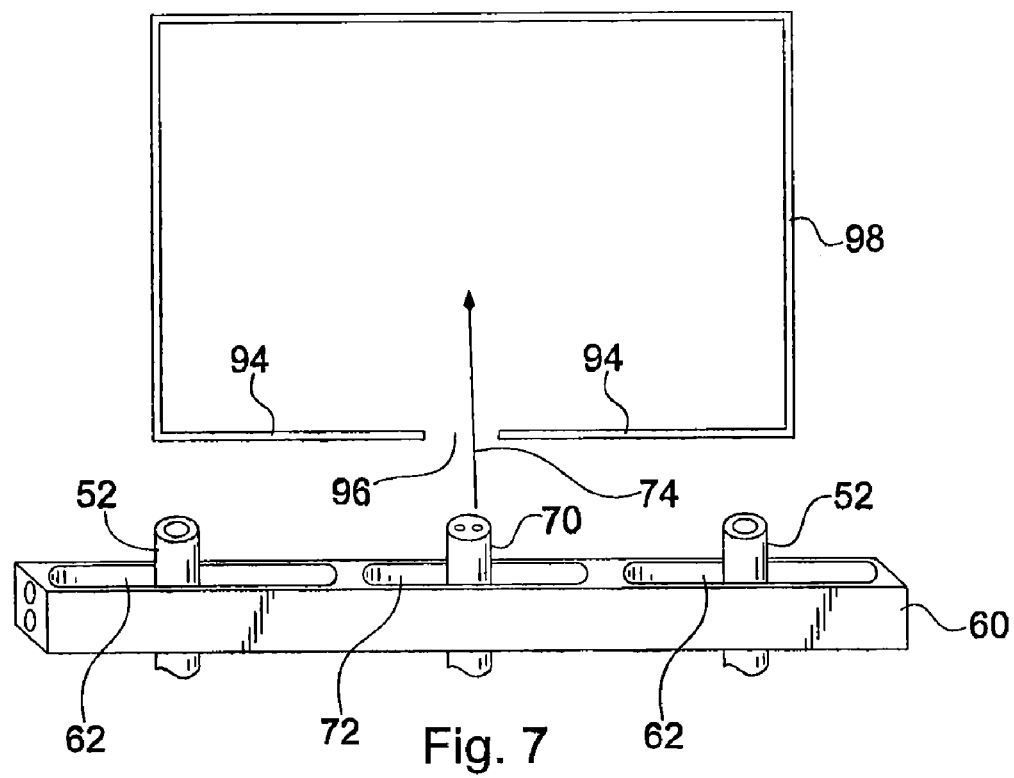

BOX INSPECTOR

TECHNICAL FIELD

The present invention relates generally to inspection equipment and, more specifically, to a completely automated system for inspecting, detecting defects in, and sorting boxes.

BACKGROUND OF THE INVENTION

In the field of industrial automation, inspection systems have long been applied to inspect, detect defects in, and sort containers such as boxes. Conveyers are often used to deliver the containers to and remove them from the inspection system. For example, U.S. Pat. No. 4,165,939 issued in 1979 and discloses an inspection system for detecting dimensional tolerances, shape, and cosmetic defects in containers. A conveyer carries the containers past an inspection point where at least one focused beam of radiant energy traverses the surface of the container at a steep angle. The pattern of the surface is detected and evaluated by optical imaging techniques to determine the acceptability of the inspected container while maintaining a capability of making allowances for manufacturing tolerances of the relative position of the area under inspection with respect to a given reference point of the container. The inspection process is initiated and terminated depending upon the translational position of the container with respect to the inspection system.

U.S. Pat. No. 5,802,803 discloses a case packer comprising an inspection unit, a packing unit, and a sorting unit. The inspection unit is disposed on an upstream side of a path of transportation for packaged products for inspecting each of the products being transported on the path and thereby distinguishing defective products from normal products. The packing unit is disposed on a downstream side of the path for packing a specified container simultaneously with products delivered to the container in a plurality of rows on the path. Finally, the sorting unit is disposed between the inspection unit and the packing unit along the path for discharging the defective products away from the path and arranging the normal products in the plurality of rows on the path.

Optoelectronic sensors for detecting and locating objects are valuable in a wide variety of fields, including industrial automation. Photoelectric sensors, which comprise a type of optoelectronic sensor, have long been used to detect and locate objects. For example, U.S. Pat. No. 3,750,877 issued in 1973 and discloses an apparatus for inspecting the walls of containers. The apparatus uses a light-emitting device, a photosensitive device, and a high-speed rotatable carrier for serially moving each of the containers between such devices to enable any undesirable opening (i.e., an edge crack) in the walls of the containers to be detected by light passing through the walls to energize the photosensitive device which in turn actuates a mechanism to reject the particular defective container.

U.S. Pat. No. 5,141,111 is titled "System and Method for Inspecting and Rejecting Defective Containers." The system includes a plurality of reflective infrared sensors, an electronic logic control, and a container-removal device. The system assesses the quality of the flange of the container and senses the height of the container by sensors irradiating the flange portion of the container with narrow beams of infrared light at varying heights and receiving radiation reflected from the flange portion. The acceptability of the container is determined by the quantum of reflected radiation received by the sensors. Unacceptable containers are removed by a high-speed pneumatic cylinder.

U.S. Pat. No. 6,757,420 is titled "Inspection Device for Packages" and discloses an automatic inspection device. The device determines whether sealed blister packages, consisting of a blister container and a cover film, are free of defects in the blister container, the sealing seam, or the perforation. At least two light sources are arranged at a certain distance from one another and each emit a light bundle at a predetermined wavelength range, whereby the emission maxima of the two light sources are offset in relation to one another. The light sources are arranged such that the packages are vertically illuminated. The light reflected by the packages is recorded by a CCD camera and the digital images are stored in a computer, so that they are available in a computer-supported image-processing and documentation system.

Many entities have worked toward improving the conventional inspection systems. For example, Cognex Corporation is a manufacturer of machine vision systems, software, and sensors used in automated manufacturing to inspect and identify parts, detect defects, verify product assembly, and guide assembly robots. Cognex is headquartered in Natick, Mass. One particular Cognex system is disclosed in U.S. Patent Publication No. 2008/0310676 titled "Method and System for Optoelectronic Detection and Location of Objects."

Disclosed in the patent publication is a system for optoelectronic detection and location of moving objects. The system captures one-dimensional images of a field of view through which objects may be moving, and makes measurements in those images. The system selects from among those measurements those that are likely to correspond to objects in the field of view, makes decisions responsive to various characteristics of the objects, and produces signals that indicate those decisions. The disclosed system is touted as providing excellent object discrimination, electronic setting of a reference point, no latency, and high repeatability.

Machine vision systems such as those of Cognex can cost many thousands of dollars and include extremely complex components such as cameras, lenses, and digital processors. Generally, machine vision systems apply computer vision to industry and manufacturing. Whereas computer vision is mainly focused on machine-based image processing, machine vision most often also requires digital input/output devices and computer networks to control other manufacturing equipment such as robotic arms. Machine vision systems combine computer science, optics, mechanical engineering, and industrial automation.

Defective boxes can damage on-line production machines, cause of loss of product, and result in unusable, or even dangerous, boxes. Nevertheless, no simple, cost-effective, automatic system exists to detect certain types of defects in shipping boxes. Boxes may be manually inspected, of course, for defects and proper dimensions. Manual inspection has several disadvantages. For example, modern production lines, such as container manufacturing and filling operations, typically operate at very high speeds. Manual inspection of boxes moving at such speeds is difficult.

Therefore, there remains a need in the art for an improved system for inspecting boxes that overcomes the shortcomings of conventional inspection systems. To overcome the shortcomings of the current solutions applied to inspect boxes, a new box inspector is provided. An object of the present invention is to inspect boxes filled with items to determine the presence of defects in the boxes or the absence of items from the boxes. Another object is to simultaneously inspect a box for one or more of dimensional conformity, gaps between flaps, and the presence of items within the box.

Yet another object is to decrease the cost and complexity of the machinery used to inspect boxes. A related object is to provide a system that does not scan the box under inspection. A further related object is to use fixed position beams to inspect the boxes. An additional object is to identify unacceptable boxes without disrupting production speeds or interrupting conveying equipment. It is still another object of the present invention to correlate the translational speed of the box under inspection with the inspection system. A related object is to permit adjustment of the box inspector to meet the specific requirements of a particular application.

BRIEF SUMMARY OF THE INVENTION

To achieve these and other objects, and to meet these and other needs, and in view of its purposes, the present invention provides a box inspector for detecting at an inspection station an unacceptable skew in, an item missing from, and an unacceptable gap in a box having a leading edge, a height, a width, a bottom opening closed by flaps defining the gap, and an open top. The box inspector includes at least two pairs of aligned emitters and receivers located in fixed positions at the inspection station and creating two spaced and parallel radiation beams through which the box to be inspected passes, each receiver generating a signal when the beam to be received by the receiver from the corresponding emitter is cut by the leading edge of the box. The box inspector further includes at least two item present sensors corresponding to the number of items adapted to be located in a single row within the box, the item present sensors being located in fixed positions at the inspection station, directing radiation toward the open top of the box, receiving radiation reflected from any items present in the box, and generating an item absent signal when an item is missing from the box. The box inspector still further includes a gap detect sensor located in a fixed position at the inspection station, under the box and between the flaps of the box when the box arrives at the inspection station, the gap detect sensor emitting radiation toward the box, detecting radiation reflected from the gap, and generating an unacceptable gap signal when the gap is larger than a predetermined gap size. (By "predetermined" is meant determined beforehand, so that the predetermined gap size is determined, i.e., chosen or at least known, before the box is inspected.) A box present sensor directs radiation toward the box, receives radiation reflected from the box, and generates a box present signal when the radiation indicates the presence of a box at the inspection station. Also included in the box inspector is a controller (a) receiving signals from the receivers, the item present sensors, the gap detect sensor, and the box present sensor, (b) having a skew tolerance timer with a preset value, (c) generating an indication that the box is unacceptably skewed when the signals received from the respective receivers exceed the preset value, (d) generating an indication that an item is missing from the box when the signals received indicate that an item is missing and a box is present, and (e) generating an indication that an unacceptable gap exists in the box when the signals received indicate that the gap is larger than the predetermined gap size and a box is present.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 6 illustrates the components of the box inspector used to detect a gap between the flaps used to close the bottom opening of a box, highlighting an acceptable gap;

FIG. 7 illustrates the components shown in FIG. 6, highlighting an unacceptable gap;

DETAILED DESCRIPTION OF THE INVENTION

Figure 1:
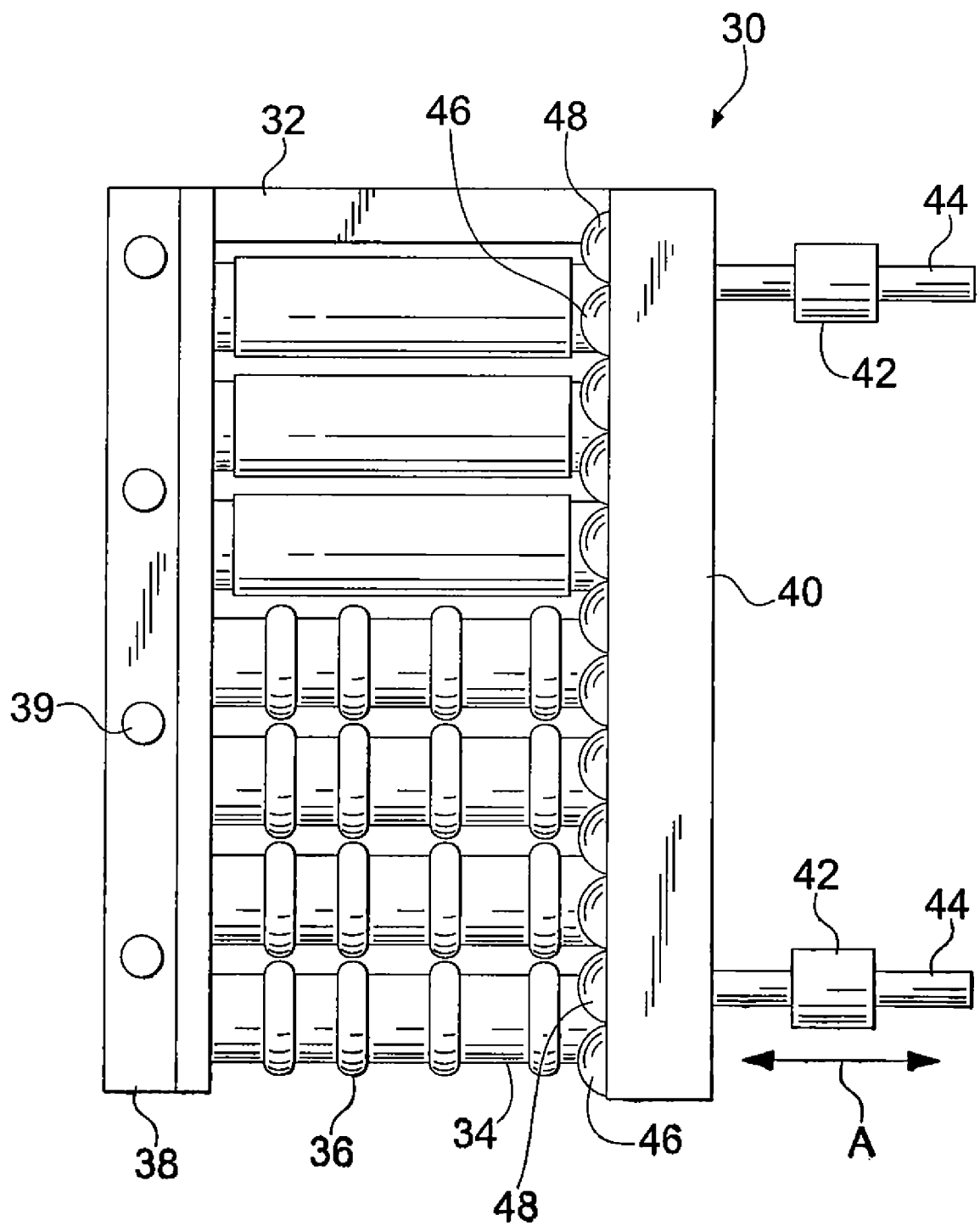
FIG. 1 is a top view of the conveyor system of the box inspector according to an exemplary embodiment of the present invention.

Products such as plastic bottles manufactured by molding machines are typically shipped in containers such as rectangular cardboard boxes, each box carrying a specified number of bottles. Conveyors sequentially transport the bottles from a molding machine, and a packing mechanism automatically arranges the bottles inside a given box. The bottles are typically arranged in a plurality of rows of two or three bottles per row.

With general reference to the figures, the box inspector 100 of the present invention is designed to detect one or more defects in a box 98. Specifically, and by way of example, the box inspector 100 can detect any one or more of three defects: boxes 98 that are out-of-square (i.e., skewed boxes), boxes 98 that are missing contents such as bottles 64, and boxes 98 that have excessive gaps 96 between the flaps 94 of the boxes 98. The problems caused by the defect of missing contents from a box 98 are perhaps obvious.

The problems caused by skewed boxes 98 may be less obvious, but are numerous. The shape of boxes 98 typically permits stacking, and skewed boxes 98 fail to stack properly. The items that should fit within the box 98 may not pack properly inside a skewed box 98. Further, the items may jam upon insertion into a skewed box 98.

Boxes 98 typically have four flaps 94—one on the leading end, one on the trailing end, and one on each side—which are folded to create the bottom of the box 98. Often, a small gap 96 exists after folding of the flaps 94. Problems arise if the gap 96 is too wide. For example, the structural integrity of the box 98 may be compromised and, especially when the box 98 carries heavier items, the box 98 may be unable to contain the items. In addition, the boxes 98 are often manipulated or handled using suction cups; an overly large gap 96 risks a loss of suction such that the handling system may drop the box 98.

The term "box" certainly includes the typical rectangular unit made of cardboard and having foldable flaps to close the top opening, the bottom opening, or both openings in the box 98. The principles of the present invention are not limited to such a narrow definition, however, and the box inspector 100 can inspect and detect defects in similar units including packages, sachets, containers, cartons, envelopes, and others.

A. Conveyor and Guide Rail Setup

The boxes 98 to be inspected are moved in series via a transport system (e.g., on a moving belt conveyor or conveyor system 30) to an inspection station. The conveyor system 30 operates to move the boxes 98 in a spaced relation through the inspection station where the boxes 98 are inspected. All of the inspections performed by the box inspector 100 rely on the boxes 98 being presented to the inspection station parallel to the conveyor 32 and perpendicular to radiant energy emitted by certain components of the box inspector 100, and being moved through the inspection station smoothly and evenly. This is an important aspect of the box inspector 100, and the precision and repeatability of the inspections performed will be determined by how well the conveyor system 30 is set up.

Referring now to the drawing, in which like reference numbers refer to like elements throughout the various figures that comprise the drawing, FIG. 1 is a top view of the conveyor system 30 of the box inspector 100 according to an exemplary embodiment of the present invention. Conventional conveyor systems are not precision pieces of equipment, but they can be modified to provide the required level of repeatability to function as a component of the box inspector 100. Time is the variable used as the tolerance to adjust sensitivity on all of the inspections. As such, all of the rollers 34 of the conveyor 32 must turn evenly to provide a steady, smooth motion for the box 98 through the inspection station. If the pulleys that drive the rollers 34 are not fixed (i.e., they cannot spin on the shaft) to the drive shaft, it is necessary to attach them with epoxy or set screws. If set screws are used, it is recommended to use the smallest possible screws so that the screws do not protrude from the pulley and wear on the drive band. It is also recommended to use Loctite® adhesive, available from Henkel Corporation of Rocky Hill, Conn., or a similar thread-locking compound on the screws so that the screws do not back out.

All of the rollers 34 and roller bearings must be in good condition so they turn easily without binding. Traction between the rollers 34 and the boxes 98 is increased by the use of rubber sleeves or O-rings 36. The increased traction allows the conveyor motor to be slowed (e.g., from a conventional 60 Hz rate to about 18 Hz by the use of a variable frequency drive) while the conveyor 32 still moves the boxes 98 in a positive and even manner. By slowing the conveyor 32, the amount of time the boxes 98 are at the inspection station is increased. The longer it takes for boxes 98 to pass through the inspection station, the more accurate is the inspection.

For example, if it takes 10 milliseconds (1 millisecond=$\frac{1}{1000}$ or 0.001 seconds) for a box 98 to pass through the skewed box detect inspection, the tolerance must be set between 1-10 milliseconds, which does not leave much room for adjustment. If it takes 100 milliseconds to pass through the inspection station, however, the tolerance can be set between 1-100 milliseconds. Ideally, the conveyor 32 should be slowed as much as possible without affecting the amount of boxes 98 that are processed. Slowing the conveyor motor also has the benefit of using less electricity, which achieves cost savings, and prolonging the life of associated moving parts such as rollers 34 and drive bands.

In order to present the boxes 98 to the box inspector 100 in the same position, guide rails are incorporated in the conveyor system 30. A fixed guide rail 38 is provided on one side of the conveyor 32. The fixed guide rail 38 is fixed with respect to, and parallel to, the conveyor 32 and the box inspector 100. The guide rail 38 may be fixed by pins 39 or any other suitable fastener as would be known to an artisan. An adjustable guide rail 40 is provided on the opposite side of the conveyor 32. The adjustable guide rail 40 is adjustable for different box widths, but parallel to the conveyor 32 and the box inspector 100. One or more adjusters 42 move along a track 44 in the direction of arrow A to accommodate boxes 98 of different sizes.

A plurality of bearings 46, 48 can be provided on one or both of the guide rails 38, 40 to decrease friction between the guide rails 38, 40 and the sides of the boxes 98. (Bearings 46, 48 are shown in FIG. 1 only on the adjustable guide rail 40 for simplicity, but bearings 46, 48 could also by provided on the fixed guide rail 38.) The bearings 46, 48 can be positioned at different heights so that they contact the boxes 98 at different locations. In the example embodiment illustrated in FIG. 1, lower bearings 46 alternate with upper bearings 48. By reducing the drag on the boxes 98, the guide rails 38, 40 can be set a little tighter, increasing the accuracy of inspections. If different boxes 98 are to be inspected, it is recommended to use positive stops for each setup. By doing this, changeover time is reduced and repeatability is increased.

Figure 2:
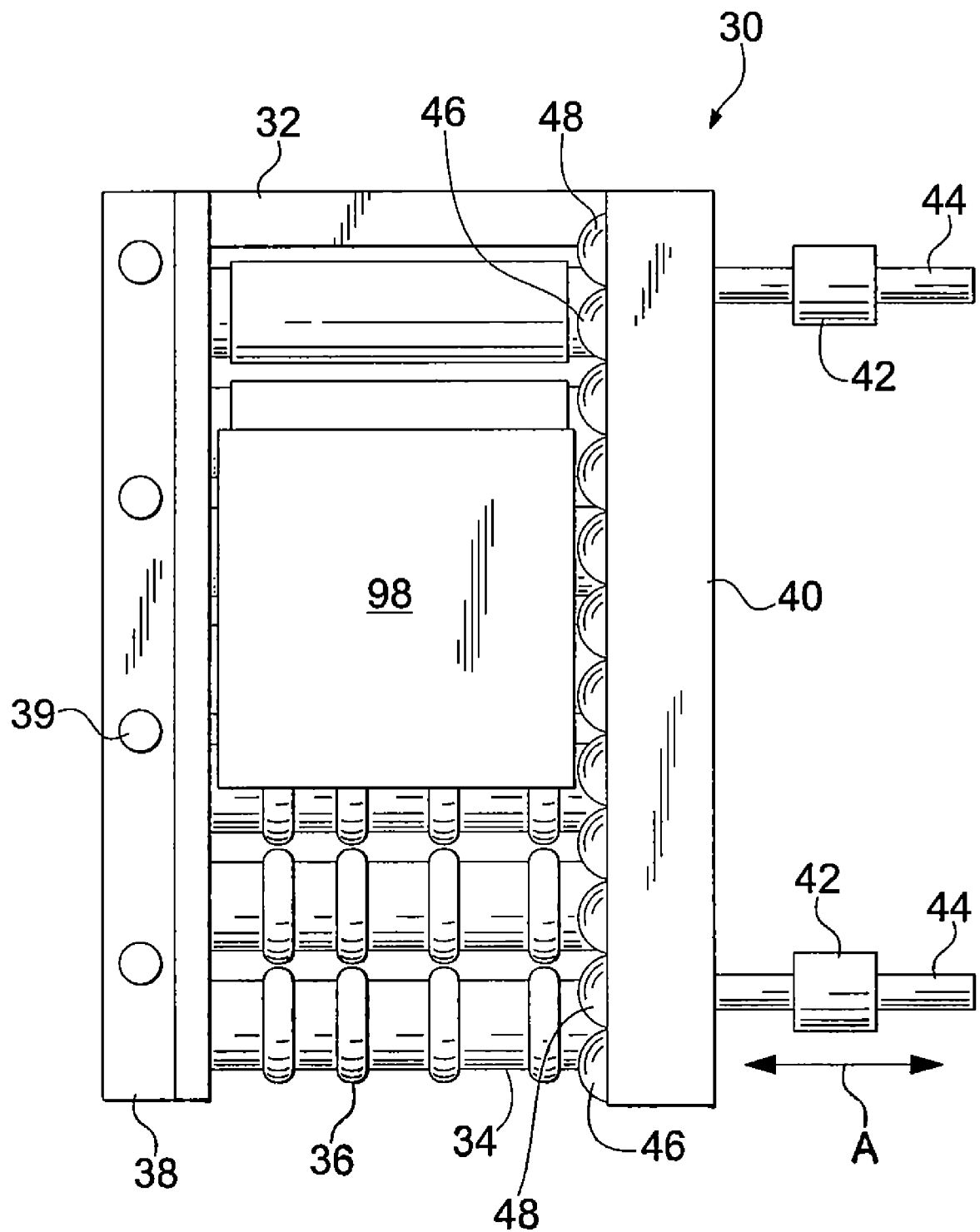
FIG. 2 is a top view of the conveyor system shown in FIG. 1 with a box traveling along the conveyor.

FIG. 2 illustrates the conveyor system 30 of FIG. 1 with a box 98 traveling along the conveyor 32. The boxes 98 are kept parallel with the conveyor 32 and inspection unit using the fixed guide rail 38 and the adjustable guide rail 40. Bearings 46, 48 on the adjustable guide rail 40 contact the boxes 98 as needed to assure the proper orientation and smooth, even travel along the conveyor 32.

B. Out-Of-Square (Skew) Detection

Photoelectric sensors typically operate by emitting a beam of light and detecting light received. Such sensors are available in a variety of configurations. In one configuration, an emitter and a receiver are placed at opposite ends of a path, so that anything crossing the path that is not transparent breaks the beam of light; an object is detected when the receiver sees very little light. The placement of the emitter and receiver determines the path and thereby the location at which an object is detected. The application is constrained to insure that only desired objects cross the path, and so that determining the location of an edge of the object is all that is needed.

In a second configuration, an emitter and a receiver are placed in one location, with a retro-reflector placed at the opposite end of a path that reflects the beam from the emitter back to the receiver. This configuration is similar to the first configuration, but is more convenient to install because all of the required wiring is done at only one end of the path instead of at both ends.

In a third configuration, an emitter and a receiver are placed in one location, and the emitter emits a focused beam of light so that anything sufficiently reflective crossing in front of the beam reflects the beam back to the receiver. An object is detected when the receiver sees an amount of light above some predefined threshold. The placement of the emitter-receiver unit determines the location of the beam and thereby the location at which an object is detected. The use of a focused beam makes this location relatively precise, and reduces the chances of misdetecting objects in the background because the beam will be out of focus. The objects and their environment are constrained so that the reflected light exceeds the threshold only when desired objects are in the desired location.

A fourth configuration is a variation of the third in which a diffuse beam of light is used instead of a focused beam. The diffuse beam makes it easier to detect objects whose positions are not well constrained, but decreases the precision of the location at which objects are detected and increases the chances that a detection will occur when no desired object is in front of the beam.

Photoelectric sensors typically provide a simple signal to indicate that an object has been detected, and to indicate its location. Such a signal has two states, which might be called "present" and "absent." In the first and second configurations, for example, the signal would be in the "present" state when little light is detected by the receiver. In the third or fourth configuration, however, the signal would be in the "present" state when light above a threshold is detected by the receiver. Usually a photoelectric sensor is used to detect specific objects and locate them at a specific position, for example to detect boxes moving down a conveyer belt and indicate the time at which the leading edge of such a box has reached a certain reference point.

Although the embodiments described and illustrated include fiber optics, a person of ordinary skill in the art would understand that lasers could be substituted for the fiber optics if greater accuracy is required. The terms "emitter(s)" and "receiver(s)" therefore include both lasers and fiber optics, as well as other structural equivalents as would be known to the artisan.

Figure 3:
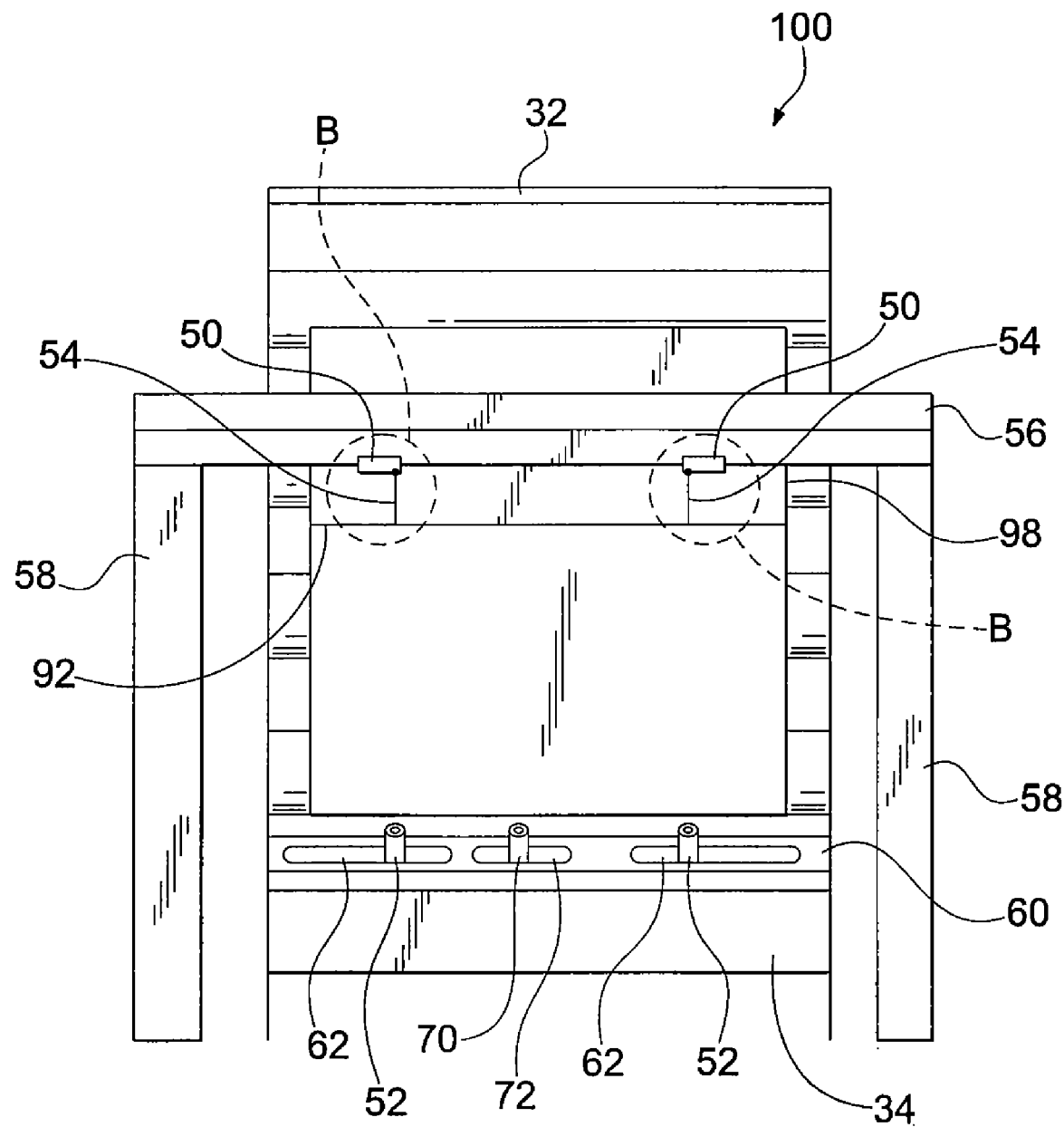
FIG. 3 illustrates the components of the box inspector used to detect a box that is out-of-square or skewed.

FIG. 3 illustrates the components of the box inspector 100 used to detect a box 98 that is out-of-square or skewed. Although more pairs could be used, the illustrated embodiment of the box inspector 100 has two pairs of fiber optic emitters 50 and receivers 52 to create two vertical beams 54 through which the boxes 98 must pass. One beam 54 is on the left side of the box 98 and the other beam 54 is on the right, as highlighted by the circular fields labeled "B" in FIG. 3. As illustrated, the emitters 50 are mounted on a top frame 56, which is supported by a pair of legs 58, and are adjustable from side to side. The receivers 52 are mounted on a sensor bar 60 located between the rollers 34 of the conveyer 32. The sensor bar 60 has slots 62 to allow side-to-side adjustment of the receivers 52. Although illustrated with the receivers 52 mounted on the sensor bar 60 below the boxes 98 and with the emitters 50 mounted on the top frame 56 above the boxes 98, the location of the emitters 50 and receivers 52 could be reversed.

Ideally, the emitters 50 and receivers 52 should be mounted as close to the sides of the boxes 98 as possible, where the difference in the time the edges 92 of the boxes 98 cut the fiber optic beams 54 is the greatest. The emitters 50 must be aligned with the receivers 52 for proper operation. The emitters 50 produce a red circle that must be centered on the receiver 52. If a box 98 is substantially square, as shown in FIG. 3, both beams 54 will be cut by the box 98 at approximately the same time.

Figure 4:
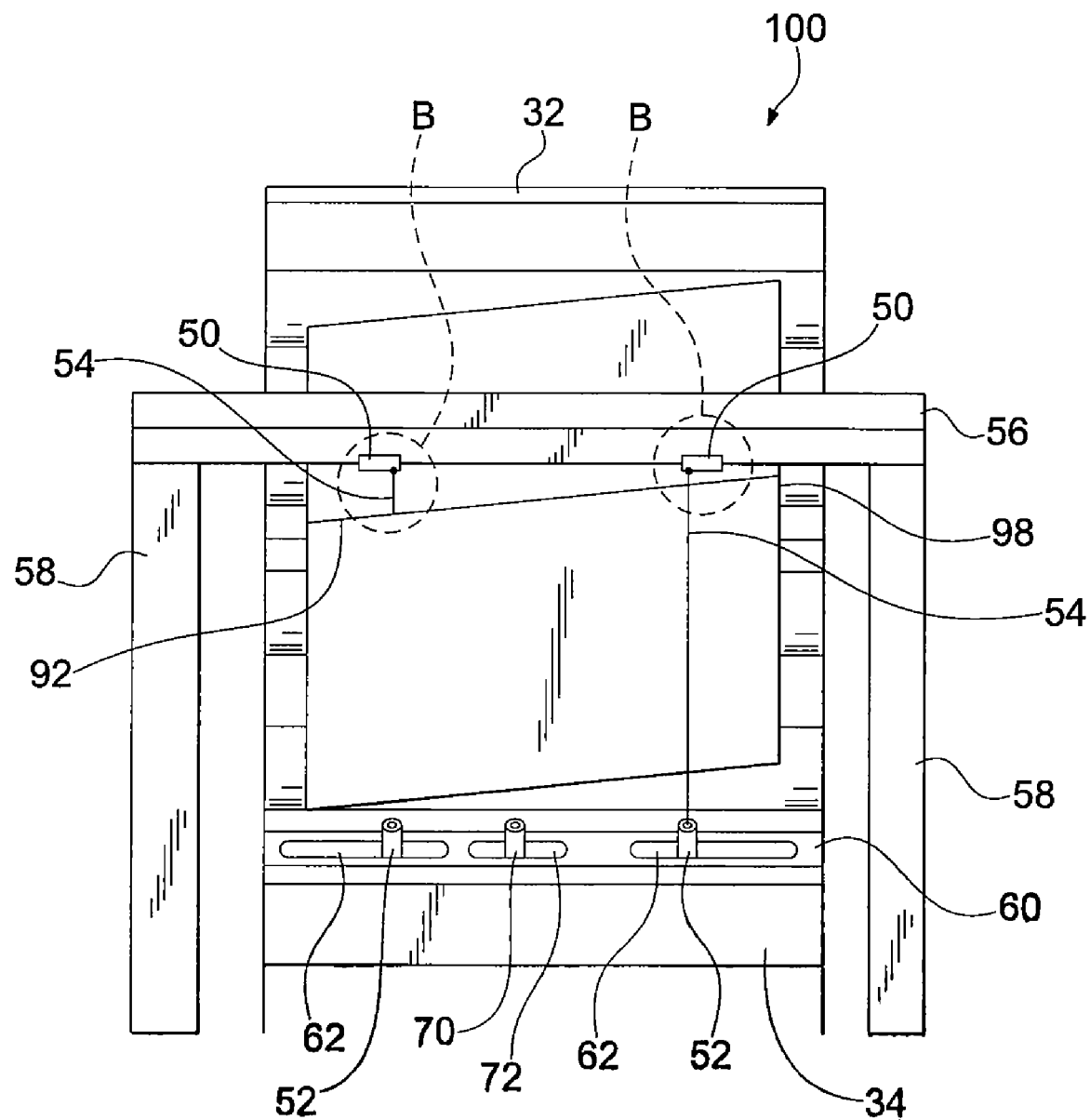
FIG. 4 illustrates the components shown in FIG. 3 with a skewed box under inspection.

If a box 98 is not substantially square, as shown in FIG. 4, one side of the box 98 will cut its beam 54 before the other side does. Upon interception of the beam 54 by the box 98, a signal is generated by the respective one of the receivers 52 and is conveyed to a programmable logic controller (PLC) 6 (see FIG. 9). The PLC 6 will start a timer when one beam 54 is cut and the other beam 54 is not. If the timer reaches its preset value (skew tolerance) before the other beam 54 is cut, the box 98 will be flagged as out of square. Therefore, when setting the skew tolerance timer, the larger the entered value (in milliseconds) the less sensitive the inspection will be and vice versa.

If presently available circuitry, whether analog, digital or hybrid, is used, the speed of signal generation, analysis, and comparison is extremely high. In fact, the time period required for these purposes is only a small fraction of the time required to move the box 98 past beams 54. Therefore, it becomes evident that operation of the box inspector 100 of the present invention is relatively independent of the speed of the conveyer 32 and will accommodate most presently known speeds for such conveyers 32. By adjustably mounting the emitters 50 and the receivers 52 (i.e., the sensors), boxes 98 of various dimensions can be inspected.

C. Missing Bottle Detection

Figure 5:
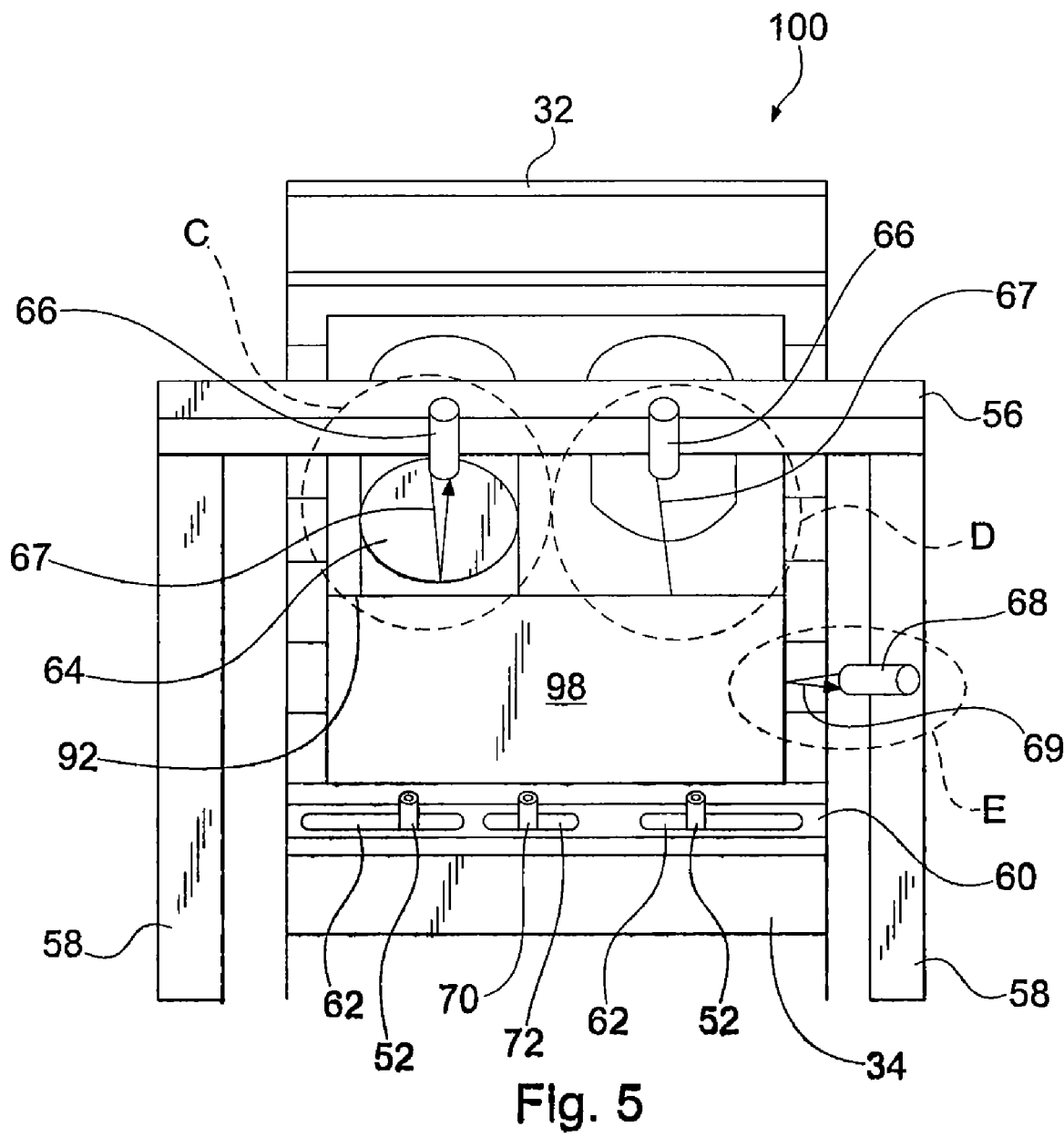
FIG. 5 illustrates the components of the box inspector used to detect a box that should have, but is missing, a bottle or other item desired to be loaded in the box.

FIG. 5 illustrates the components of the box inspector 100 used to detect a box 98 that should have, but is missing, a bottle 64 or other item desired to be loaded in the box 98. For the embodiment illustrated, in which the box 98 should have two bottles 64 per row within the box 98, the components include two diffused photo electric bottle present sensors 66 and a diffused photo electric box present sensor 68. (More bottle present sensors 66 would be required if there were more bottles 64 per row.) The bottle present sensors 66 are positioned on the top frame 56 and direct radiation 67 downward toward the top of the open box 98 as highlighted by the circular fields labeled "C" and "D" in FIG. 5. When the radiation 67 reflects from a bottle 64 and returns to the bottle present sensor 66, as illustrated in field "C," the bottle present sensor 66 sends a "bottle present" signal to the PLC 6. In contrast, when the radiation 67 is not reflected from a bottle 64 and returned to the bottle present sensor 66, as illustrated in field "D," the bottle present sensor 66 sends a "bottle absent" signal to the PLC 6.

The bottle present sensors 66 should be adjusted as close to the bottles 64 as possible without causing any interference with the tallest box 98 to be inspected. Ideally, this height should be left in the same position for all boxes 98 to be inspected, but if the height difference between the tallest and shortest boxes 98 is too great, it may have to be adjusted on changeovers. If the height is adjusted on changeovers, it is recommended to use stops to set the height for each product.

The box present sensor 68 is positioned on one of the legs 58 and directs radiation 69 horizontally toward the side of the box 98 as highlighted by the circular field labeled "E" in FIG. 5. When the radiation 69 reflects from a box 98 and returns to the box present sensor 68, as illustrated in field "E," the box present sensor 68 sends a "box present" signal to the PLC 6. In contrast, when the radiation 69 is not reflected from a box 98 and returned to the box present sensor 68, the box present sensor 68 sends a "box absent" signal to the PLC 6 (which may be, for example, no signal at all). The sensitivity of the box present sensor 68 may be adjusted by a potentiometer on the body of the box present sensor 68.

If the box present sensor 68 detects a box 98 while either or both bottle present sensors 66 do not detect a bottle 64, the box 98 will be flagged as missing a bottle 64. Because there may be space between the bottles 64 in the boxes 98 being inspected, a missing bottle tolerance timer is used to filter out false rejects. The missing bottle tolerance timer is the maximum amount of time that a bottle present sensor 66 can go without detecting a bottle 64 while the box present sensor 68 detects a box 98 and not flag the box 98 as missing a bottle 64.

For example, if a box 98 with all bottles 64 present goes through the inspection station and one of the bottle present sensors 66 detects a gap between two of the bottles 64 for 10 milliseconds, the box 98 should not be flagged as missing a bottle 64. If a box 98 missing a bottle 64 causes a bottle present sensor 66 to detect a gap of 100 milliseconds, however, that box 98 should be flagged as missing a bottle 64. So, in this example case, the missing bottle tolerance timer should be set somewhere between 10 and 100 milliseconds to flag any boxes 98 missing bottles 64, but not flag boxes 98 due to normal gaps between bottles 64.

The bottle present sensors 68 can be "taught" to tell the difference between a box 98 having bottles 64 and a box 98 lacking bottles 64. To do so, samples of each situation are provided. The teaching method is described below in Section E.

D. Unacceptable Gap Detection

FIG. 6 illustrates the components of the box inspector 100 used to detect a gap 96 between the flaps 94 used to close the bottom opening of the box 98. The gap detect components include a diffused fiber optic gap detect sensor 70 to check for unacceptable gap size. The gap detect sensor 70 should be adjusted below the gap 96 between the bottom flaps 94 as close as possible without being contacted by any boxes 98. As illustrated in the embodiment of the box inspector 100 shown in FIG. 6, the gap detect sensor 70 is mounted on the sensor bar 60 located between the rollers 34 of the conveyor 32 along with the receivers 52. The sensor bar 60 has a channel 72 to allow side-to-side adjustment of the gap detect sensor 70.

The gap detect sensor 70 emits radiation, for example light 74, toward the box 98 and its gap 96. An acceptable gap 96 should reflect enough light 74 back to the gap detect sensor 70 so that the gap detect sensor 70 detects that the width of the gap 96 is acceptable. This situation is illustrated in FIG. 6. An unacceptable gap 96 will allow more light 74 to pass through the gap 96 and less light 74 will be reflected back to the gap detect sensor 70, so the gap detect sensor 70 detects that the gap 96 is unacceptable. This situation is illustrated in FIG. 7.

In other words, when the gap 96 is smaller, more light 74 is reflected back to the gap detect sensor 70 and vice versa. If an acceptable gap 96 is too large, the gap detect sensor 70 can be positioned so that it is hidden by one flap 94 on an acceptable gap 96, but exposed to the gap 96 on an unacceptable gap 96. The gap detect sensor 70 can be taught to tell the difference between an acceptable and unacceptable gap 96 if samples of each are provided. The teaching method is described below in Section E.

If the gap detect sensor 70 detects an unacceptable gap 96 at the same time that the box present sensor 68 detects a box 98, the box 98 will be flagged as having an unacceptable gap 96. The gap detect tolerance timer is the amount of time that the gap detect sensor 70 can detect an unacceptable gap 96 while the box present sensor 68 detects a box 98 before it is flagged for being defective. The higher this setting (in milliseconds) the less sensitive will be the gap detection and vice versa.

Figure 8:
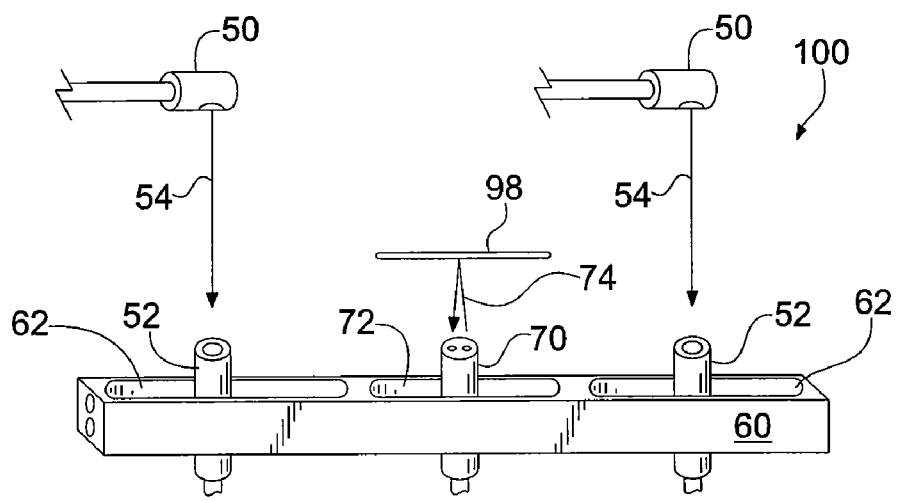
FIG. 8 illustrates the box inspector, according to another exemplary embodiment of the present invention, which combines the components used to detect skewed boxes with the components used to detect gaps.

As mentioned above, the box inspector 100 of the present invention is designed to detect any one or more of three defects: skewed boxes 98, boxes 98 that are missing contents such as bottles 64, and boxes 98 that have excessive gaps 96 between flaps 94 of the boxes 98. The components of the box inspector 100 designed to detect each of these defects are highlighted, respectively, in Sections B, C, and D above. The box inspector 100 can incorporate one, any combination of two, or all three aspects of detection. For example, as illustrated in FIG. 8, the box inspector 100 combines the components used to detect skewed boxes 98 with the components used to detect gaps 96.

E. Operator Interface

Figure 9:
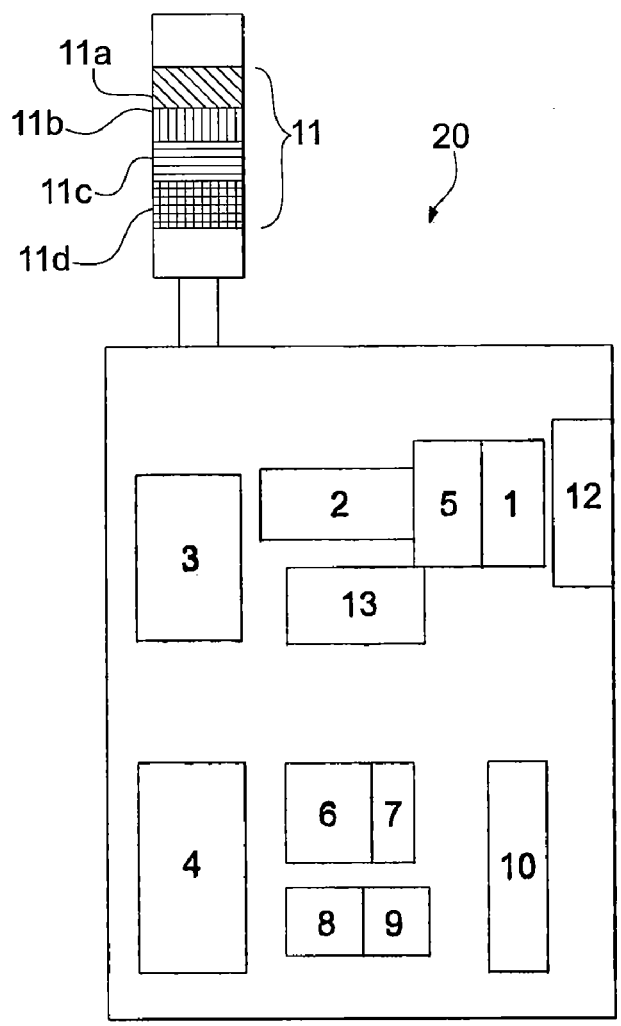
FIG. 9 is a schematic illustration depicting the components of an electrical box used to operate the box inspector and to provide a user interface according to an exemplary embodiment of the present invention.

As illustrated schematically in FIG. 9, an electrical box 20 is included to operate the box inspector 100 and to provide a user interface. The electrical box 20 may include a number of components, such as a power disconnect 1, fuse blocks 2, a transformer 3 (e.g., a 480 volt to 110 volt transformer), a variable frequency drive 4 (e.g., a 480 volt three-phase variable frequency drive), a power supply 5 (e.g., 24 volts), the PLC 6, a PLC output module 7, PLC input-output terminals 8, amplifiers 9 (e.g., three fiber optic amplifiers to detect left-left skew, center-right skew, and right gap, respectively), terminal blocks 10, a series of alarms or indicators 11, a fan 12, and a touch screen 13. Preferably, the electrical box 20 is located proximate the conveyor system 30 (i.e., at least within visual sight of the conveyor system 30 if not adjacent to the conveyor system 30). The electrical box 20 may communicate with one or more of the conveyor system 30, the adjusters 42, the receivers 52, the bottle present sensors 66, the box present sensor 68, and the gap detect sensor 70 through wires connecting the electrical box 20 to those components or wirelessly.

The touch screen 13 may be located, for example, on the front exterior of a door of the electrical box 20. By providing a user interface, the touch screen 13 allows for adjustment of various settings without requiring the use of PLC software. If there is a power outage, these settings may have to be re-entered, so it is recommended to keep a setup sheet with all settings near the electrical box 20. The touch screen 13 may display statistics such as the total number of boxes 98 inspected and rejected.

An "F1" button positioned below a conveyor icon serves as a reset button to restart the conveyor 32 or release the stop brake after a defective box 98 has been removed from the conveyor 32. A remote reset button may be located on the opposite side of the conveyor 32 which serves the same purpose. An "F2" button below an alarm clock icon resets the boxes inspected and rejected counters back to zero. An "F3" button below a charts icon opens a statistics screen. The statistics screen has statistics on rejects for each individual inspection. To return to the main menu, the user presses a button under a home icon.

An "F4" button below a box icon opens a product selection screen. The product selection screen allows the user to select the product they will be running through the box inspector 100. If multiple products are to be run, "recipes" with the ideal settings for each product can be set up and saved. The settings for the product to be run will automatically be loaded into the PLC 6 when that product is selected. To return to the main menu, the user presses the button below the home icon.

An "F5" button below a tools icon opens a tools screen. The tools screen is where the tolerances and settings may be accessed. To change a setting, the user touches the setting on the display. This action will open a numeric keypad with which to enter the new value, followed by an "ent" (enter) button. The new value should be reflected in the display below the desired parameter.

If desired, password protection can be assigned to various screens and different access levels can be assigned to different levels of users. For example, an operator level may view and reset counters, but could not change products or adjust tolerances. A mechanic level may view and reset counters as well as change product selection, but could not adjust inspection tolerances. A supervisor level would be able to do all of the above and adjust inspection tolerances.

The indicators 11 are provided to convey information from the box inspector 100 to the user. The indicators 11 may be any suitable audio-visual devices as would be know to the artisan. By way of example, the indicators 11 are illustrated in FIG. 9 as stacked light-emitting diode (LED) indicators 11a, 11b, 11c, and 11d. Each stacked indicator may be assigned a different color; therefore, indicator 11a may be green, indicator 11b may be red, indicator 11c may be blue, and indicator 11d may be yellow. The indicators 11 will sound an audible alarm and turn on a colored light if a defect is detected. Each color corresponds to a different defect (red may indicate an unacceptable box skew, blue may indicate a missing bottle 64, and yellow may indicate an unacceptable gap 96) and green may indicate the box inspector 100 is online and inspecting. The indicators 11 will turn off after the defective box 98 is removed and the reset button is pressed.

The bottle present sensors 68 (see FIG. 5) can be "taught" by placing a box 98 with bottles 64 underneath the sensors 68 and pressing a teach button for 2-5 seconds. The green LED indicator 11a should stay on at this point when a bottle 64 is present and turn off when bottles 64 are removed (at which point, the blue LED indicator 11c should turn on). The sensors 68 should be taught with the area of the bottle 64 furthest away from the sensor 68 (usually the base push up/gate nub area) directly underneath the sensor 68. The bottle present sensors 68 should be adjusted directly above the middle of the bottles 64. This is especially important with round bottles 64, because there is more space between the bottles 64 the farther from center the sensors 68 are located.

To teach the gap detect sensor 70, the user takes the following steps. First, a box 98 with an acceptable gap 96 is placed over the gap detect sensor 70 with the gap 96 centered over the gap detect sensor 70. Next, the user activates a "Teach 2" mode by pressing a "mode" key three times. Third, the user presses the "enter" key to start the first cycle. The teaching process is successful when a "status" LED lights up green. Then the box inspector 100 is ready for the second cycle.

In preparation for the second cycle, the user removes the sample box 98 with an acceptable gap 96 and places another box 98 with an unacceptable gap 96 directly over the gap detect sensor 70. The user then presses the "enter" key, and the second cycle begins. The teaching process is successful when the "status" LED blinks green for five seconds. At this point, the inspector box 100 is ready for use.

Although illustrated and described above with reference to certain specific embodiments and examples, the present invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges.

What is claimed:

1. A box inspector for detecting at an inspection station an unacceptable skew in, an item missing from, and an unacceptable gap in a box having a leading edge, a height, a width, a bottom opening closed by flaps defining the gap, and an open top, the box inspector comprising:
   at least two pairs of aligned emitters and receivers located in fixed positions at the inspection station and creating two spaced and parallel radiation beams through which the box to be inspected passes, each receiver generating a signal when the beam to be received by the receiver from the corresponding emitter is cut by the leading edge of the box;
   at least two item present sensors corresponding to the number of items adapted to be located in a single row within the box, the item present sensors being located in fixed positions at the inspection station, directing radiation toward the open top of the box, receiving radiation reflected from any items present in the box, and generating an item absent signal when an item is missing from the box;
   a gap detect sensor located in a fixed position at the inspection station under the box and between the flaps of the box when the box arrives at the inspection station, the gap detect sensor emitting radiation toward the box, detecting radiation reflected from the gap, and generating an unacceptable gap signal when the gap is larger than a predetermined gap size;
   a box present sensor directing radiation toward the box, receiving radiation reflected from the box, and generating a box present signal when the radiation indicates the presence of a box at the inspection station; and
   a controller (a) receiving signals from the receivers, the item present sensors, the gap detect sensor, and the box present sensor, (b) having a skew tolerance timer with a preset value, (c) generating an indication that the box is unacceptably skewed when the signals received from the respective receivers exceed the preset value, (d) generating an indication that an item is missing from the box when the signals received indicate that an item is missing and a box is present, and (e) generating an indication that an unacceptable gap exists in the box when the signals received indicate that the gap is larger than the predetermined gap size and a box is present.

2. The box inspector as recited in claim 1, further comprising:
   a conveyor having a plurality of rollers transporting the box to the inspection station;
   a fixed guide rail disposed on one side of the conveyor;
   an adjustable guide rail disposed on the opposite side of the conveyor and in parallel with the fixed guide rail; and
   at least one adjuster adapted to move the adjustable guide rail so that the distance between the fixed guide rail and the adjustable guide rail approximates the width of the box to be inspected, thereby orienting the box with respect to the inspection station.

3. The box inspector as recited in claim 2, wherein the rollers have means for increasing traction between the rollers and the box.

4. The box inspector as recited in claim 2, wherein at least one of the fixed guide rail or the adjustable guide rail has a plurality of bearings adapted to contact the box and assure proper orientation of the box at the inspection station.

5. The box inspector as recited in claim 2, wherein the conveyor operates at approximately 18 Hz.

6. The box inspector as recited in claim 1, wherein at least one of the emitters, receivers, item present sensors, gap detect sensor, or box present sensor are adjustable to accommodate boxes of different sizes.

7. The box inspector as recited in claim 1, further comprising at least one of a missing item tolerance timer filtering out false indications that an item is missing or a gap detect tolerance timer filtering out false indications that a gap is unacceptable.

8. The box inspector as recited in claim 1, further comprising means for interfacing with a user.

9. A box inspector for detecting at an inspection station an unacceptable skew in a box having a leading edge, a height, and a width, the box inspector comprising:
   a conveyor transporting the box to the inspection station;
   a fixed guide rail disposed on one side of the conveyor;
   an adjustable guide rail disposed on the opposite side of the conveyor and in parallel with the fixed guide rail;
   at least one adjuster adapted to move the adjustable guide rail so that the distance between the fixed guide rail and the adjustable guide rail approximates the width of the box to be inspected, thereby orienting the box with respect to the inspection station;
   at least two pairs of aligned emitters and receivers located in fixed positions at the inspection station and creating two spaced and parallel radiation beams through which the box to be inspected passes while being transported on the conveyor, each receiver generating a signal when the beam to be received by the receiver from the corresponding emitter is cut by the leading edge of the box; and a controller receiving signals from the receivers, having a skew tolerance timer with a preset value, and generating an indication that the box is unacceptably skewed when the signals received from the respective receivers exceed the preset value.

10. The box inspector as recited in claim 9, wherein the emitters and receivers are adjustable to accommodate boxes of different widths.

11. The box inspector as recited in claim 10, further comprising a frame on which the emitters are mounted and a sensor bar on which the receivers are mounted, the sensor bar being positioned under the conveyor and having slots permitting adjustment of the receivers.

12. The box inspector as recited in claim 9 further detecting at the inspection station an item missing from the box, wherein the box has an open top and the box inspector further comprises:
(a) at least two item present sensors corresponding to the number of items adapted to be located in a single row within the box, the item present sensors being located in fixed positions at the inspection station, directing radiation toward the open top of the box, receiving radiation reflected from any items present in the box, and generating an item absent signal when an item is missing from the box; and
(b) a box present sensor directing radiation toward the box, receiving radiation reflected from the box, and generating a box present signal when the radiation indicates the presence of a box at the inspection station; and
wherein the controller receives signals from the item present sensors and from the box present sensor, and generates an indication that an item is missing from the box when the signals received indicate that an item is missing and a box is present.

13. The box inspector as recited in claim 12 further detecting at the inspection station an unacceptable gap in the box, wherein the box has a bottom opening closed by flaps defining the gap and the box inspector further comprises:
(c) a gap detect sensor located in a fixed position at the inspection station under the conveyor and between the flaps of the box when the box arrives at the inspection station, the gap detect sensor emitting radiation toward the box, detecting radiation reflected from the gap, and generating an unacceptable gap signal when the gap is larger than a predetermined gap size;
wherein the controller receives signals from the gap detect sensor and generates an indication that an unacceptable gap exists in the box when the signals received indicate that the gap is larger than the predetermined gap size and a box is present.

14. The box inspector as recited in claim 9 further detecting at the inspection station an unacceptable gap in the box, wherein the box has a bottom opening closed by flaps defining the gap and the box inspector further comprises:
(a) a gap detect sensor located in a fixed position at the inspection station under the conveyor and between the flaps of the box when the box arrives at the inspection station, the gap detect sensor emitting radiation toward the box, detecting radiation reflected from the gap, and generating an unacceptable gap signal when the gap is larger than a predetermined gap size; and
(b) a box present sensor directing radiation toward the box, receiving radiation reflected from the box, and generating a box present signal when the radiation indicates the presence of a box at the inspection station; and
wherein the controller receives signals from the gap detect sensor and from the box present sensor, and generates an indication that an unacceptable gap exists in the box when the signals received indicate that the gap is larger than the predetermined gap size and a box is present.

15. A box inspector for detecting at an inspection station an item missing from a box having an open top, the box inspector comprising:
a conveyor transporting the box to the inspection station;
a fixed guide rail disposed on one side of the conveyor;
an adjustable guide rail disposed on the opposite side of the conveyor and in parallel with the fixed guide rail;
at least one adjuster adapted to move the adjustable guide rail so that the distance between the fixed guide rail and the adjustable guide rail approximates the width of the box to be inspected, thereby orienting the box with respect to the inspection station;
at least two item present sensors corresponding to the number of items adapted to be located in a single row within the box, the item present sensors being located in fixed positions at the inspection station, directing radiation toward the open top of the box, receiving radiation reflected from any items present in the box, and generating an item absent signal when an item is missing from the box;
a box present sensor directing radiation toward the box, receiving radiation reflected from the box, and generating a box present signal when the radiation indicates the presence of a box at the inspection station; and
a controller receiving signals from the item present sensors and from the box present sensor, and generating an indication that an item is missing from the box when the signals received indicate that an item is missing and a box is present.

16. The box inspector as recited in claim 15, further comprising a missing item tolerance timer filtering out false indications that an item is missing.

17. The box inspector as recited in claim 15 further detecting at the inspection station an unacceptable gap in the box, wherein the box has a bottom opening closed by flaps defining the gap and the box inspector further comprises:
a gap detect sensor located in a fixed position at the inspection station under the conveyor and between the flaps of the box when the box arrives at the inspection station, the gap detect sensor emitting radiation toward the box, detecting radiation reflected from the gap, and generating an unacceptable gap signal when the gap is larger than a predetermined gap size; and
wherein the controller receives signals from the gap detect sensor and generates an indication that an unacceptable gap exists in the box when the signals received indicate that the gap is larger than the predetermined gap size and a box is present.

18. A box inspector for detecting at an inspection station an unacceptable gap in a box having a bottom opening closed by flaps defining the gap, the box inspector comprising:
a conveyor transporting the box to the inspection station;
a fixed guide rail disposed on one side of the conveyor;
an adjustable guide rail disposed on the opposite side of the conveyor and in parallel with the fixed guide rail;
at least one adjuster adapted to move the adjustable guide rail so that the distance between the fixed guide rail and the adjustable guide rail approximates the width of the box to be inspected, thereby orienting the box with respect to the inspection station;

a gap detect sensor located in a fixed position at the inspection station under the conveyor and between the flaps of the box when the box arrives at the inspection station, the gap detect sensor emitting radiation toward the box, detecting radiation reflected from the gap, and generating an unacceptable gap signal when the gap is larger than a predetermined gap size;

a box present sensor directing radiation toward the box, receiving radiation reflected from the box, and generating a box present signal when the radiation indicates the presence of a box at the inspection station; and a controller receiving signals from the gap detect sensor and from the box present sensor, and generating an indication that an unacceptable gap exists in the box when the signals received indicate that the gap is larger than the predetermined gap size and a box is present.

19. The box inspector as recited in claim 18, further comprising a gap detect tolerance timer filtering out false indications that a gap is unacceptable.

20. The box inspector as recited in claim 18, further comprising a sensor bar on which the gap detect sensor is mounted, the sensor bar being positioned under the conveyor and having a channel permitting adjustment of the gap detect sensor.

* * * * *